United States Patent [19]

Shukla et al.

[11] Patent Number: 5,169,645
[45] Date of Patent: Dec. 8, 1992

[54] DIRECTLY COMPRESSIBLE GRANULES HAVING IMPROVED FLOW PROPERTIES

[75] Inventors: Atul J. Shukla, Memphis, Tenn.; Anumontri Vattanasiri, Bangkok, Thailand; Jyothi S. Nambiar, Pittsburgh, Pa.

[73] Assignee: Duquesne University Of The Holy Ghost, Pittsburgh, Pa.

[21] Appl. No.: 429,858

[22] Filed: Oct. 31, 1989

[51] Int. Cl.$^5$ ............................................ A61K 9/14
[52] U.S. Cl. .................................. 424/499; 424/501; 424/502
[58] Field of Search ............... 424/475, 476, 479, 489, 424/498, 502, 501, 499

[56] References Cited

U.S. PATENT DOCUMENTS 4,521,902  6/1985  Dunn ..................................... 424/19
4,753,800  6/1988  Mozda .................................. 424/440
4,756,911  7/1988  Drost et al. ......................... 424/468
4,888,178  12/1989  Rotini et al. ........................ 424/468

Primary Examiner—Thurman K. Page
Assistant Examiner—J. Spear
Attorney, Agent, or Firm—Webb, Burden, Ziesenheim & Webb

[57] ABSTRACT

Directly compressible, wax-containing granules having improved flow properties are obtained when waxes are admixed in the melt with certain flow improving additives, followed by cooling and granulation of the admixture. In certain embodiments of the invention, only the wax itself melts in the melt combination of the wax(es) and additives(s), and in other cases both the wax(es) and the additives(s) will both melt. In either case, the melt combination of the wax(es) with the additive(s) yields, upon cooling and granulation, a wax-containing particulate drug diluent having improved and unexpected flow properties.

2 Claims, No Drawings

DIRECTLY COMPRESSIBLE GRANULES HAVING IMPROVED FLOW PROPERTIES

FIELD OF THE INVENTION

The present invention relates to methods and formulations for improving the flow properties of particulate waxes, including pharmaceutical waxes.

BACKGROUND OF THE INVENTION

Before the 1950's, most pharmaceutical tablets were manufactured by granulating the active ingredients and diluents together with suitable binders. The purpose of doing so was to produce free flowing compressible granules well suited for tabletting in a tabletting press. For many new formulations, this cumbersome and long traditional process of granulation is now being replaced by direct compression.

Early in the development of direct compression preparation of pharmaceutical dosage forms, only a few chemicals (NaCl, NaBr, KBr and methanamine) possessed the necessary flow, cohesion and lubricating properties to form tablets. Direct compression later evolved, however, to become a process by which tablets are compressed directly from a mixture of a wide variety of specially processed fillers, lubricants and disintegrants which can flow uniformly into a die cavity.

Some of the known direct compression diluents include sugars such as fructose, maltose, dextrose and other polysaccharides, calcium gluconate, calcium carbonate, powdered oyster shells, calcium phosphate, and polymers such as microcrystalline cellulose and other cellulose derivatives. Although most of these diluents are chemically inert, many of them have certain drawbacks. The sugar-based diluents are hygroscopic and their compression property is significantly dependent on the amount of moisture present in the diluents. The calcium salts are alkaline and may cause unwanted chemical reactions with certain types of acidic drugs.

Other direct compression diluents, including waxes, are also known. Several wax formulations have been widely accepted for use in drug dosage forms. These waxes include, for example, carnauba wax, beeswax, glyceride esters, hydrogenated vegetable as well as animal oils, stearyl alcohols and their derivatives, polyethylene glycols and their derivatives, esters of fatty acids such as palmitic acid, stearic acid, oleic acid, linoleic acid, linolenic acid, etc. These waxes are usually if not always chemically inert, can impart sustained release characteristics when required and, as drug diluents, provide a level of cohesion which approaches the ideal when active agents are combined with them and compressed into dosage forms.

The disadvantage with waxes inheres in their flow properties, however. Although melted waxes have satisfactory flow properties under some circumstances, most waxes tend to clump, not flow, and as such are generally inappropriate for use in tabletting presses and similar production machinery even when attempts are made to grate or divide them. In fact, they are difficult to transfer, ship, store and dispense for this reason, also. In addition, of course, certain drugs should not be exposed even to the relatively low "melt heat" of a wax, for drug stability or other reasons. A free-flowing granulated wax is therefore the theoretical ideal as a diluent for incorporation into a compressed drug-containing matrix.

U.S. Pat. No. 4,590,062 to Jang, entitled "Dry Direct Compression Compositions for Controlled Release Dosage Forms," discloses combinations of waxes and certain additional diluents which can be direct compressed with an active agent to prepare a controlled release tablet. The waxes and additional diluents may be slugged together and granulated, and flow aid materials such as finely divided silica or talc, in amounts between 0.5 and 2% by weight, may be included to improve the flow properties of the resulting wax granules. The diluent wax-containing granules are disclosed by Jang as suitable for combination with a wide range of biological and pharmaceutical active agents.

SUMMARY OF THE INVENTION

It has been identified that wax-containing granules having improved flow properties are obtained when one or more pharmaceutically-acceptable waxes are admixed *in the melt* with one or more flow improving additives, with cooling and granulation of the admixture. In some instances only the wax portion of the admixture actually melts; in other cases the wax(es) and the flow improving additive(s) both melt. In either case, the melt combination of the wax(es) with the additive(s) yields, upon cooling and granulation, a wax-containing particulate diluent having improved and unexpected flow properties over wax diluent particles known in the art. The wax-containing granules can be compressed into matrices containing biologically active agents at relatively low compression pressures, with minimal requirement for added lubricants.

DETAILED DESCRIPTION OF THE INVENTION

The present invention is a particulate (granular) wax-containing composition, suitable for incorporation in oral and other dosage forms including pharmaceutical dosage forms, in which the particles demonstrate unexpectedly good flow properties notwithstanding the presence of wax(es) therein. The granular composition is prepared by the melt addition of one or more waxes and one or more additives, with subsequent cooling and granulation of the admixture. Although the wax(es) always melt during melt admixture, not all the suitable additive(s) necessarily melt, as discussed in greater detail below.

The waxes suitable for inclusion in the granular wax-containing composition are carnauba wax, beeswax, glyceryl esters, hydrogenated vegetable oils, hydrogenated animal fats, stearyl alcohols and their derivatives, polyethylene glycols and their derivatives, microcrystalline wax, and esters of fatty acids including palmitic acid, stearic acid, oleic acid, behenic acid, linoleic acid and linolenic acid. Suitable waxes bearing the trademarks Gelucires ®, Precirol ® and Compritol ® are available from Gattefosse Corporation, Elmsford, N.Y.; these waxes are all esters of fatty acids and are suitable for incorporation in the present granules. Precirol ® ATO-5 is glyceryl palmito-stearate; Compritol ® 888 is glyceryl behenate; and Gelucires ® 64/02 is glyceryl stearate, as examples.

Added to the wax, in the melt, are any of the following: polyethylene glycol (preferably PEG 4000 and/or PEG 8000), polyvinyl alcohol, polyvinyl pyrrolidone, polyvinyl acetate, ethylene vinyl acetate copolymer, acrylic polymers such as polymethyl methacrylate, polyethyl methacrylate, polymethacrylic acid and its esters and acrylic polymers and copolymers such as "Eudragits" and "Eudisperts", cellulose derivatives such as methyl cellulose, ethyl cellulose, cellulose acetate, cellulose acetate propionate, cellulose acetate butyrate, cellulose acetate phthalate, cellulose nitrate, hydroxypropyl cellulose, hydroxy propylmethylcellulose, sodium carboxymethylcellulose, micro-crystalline cellulose ("Avicel"), polyethylene oxide, poly(methylvinyl ether/maleic acid), carbomers, poly(methyl vinyl ether/maleic anhydride) ("Gantrez"), and vinyl chloride vinyl acetate polymers. Also suitable are the more common constituents such as finely divided silica, salt (NaCl, NaBr, KCL, KBr) and particulate sugars including sucrose, dextrose, and calcium gluconate, calcium phosphate and calcium carbonate particles, powdered oyster shells and ground bone meal. The ratio of wax(es) to additive(s) can range from 1:9 to 3:1; the constituents are melt combined, cooled and granulated. Ratios of 1:4 to 3:1 are preferred. Additives which do not melt are generally added in particle sizes ranging from submicrometer diameters (on the order of 0.5 micrometers) to 500 micrometer diameters.

Wax granules thus prepared are suitable for incorporation within a wide variety of pharmaceuticals and other matrices. They may be used to prepare oral dosage forms, suppositories or implants. They may be used as directly compressible diluents or may be remelted for any reason, including reformulation or granulation to a different particle size. They may be combined with vitamins, analgesics, antiinflammatory drugs, sedatives or tranquilizers, other neurologically active agents, hormones, diuretics, decongestants, cough and cold formulations and antihistamines, antineoplastic agents, motion sickness and antinauseant drugs, drugs which combat migraine and malaria, antiasthma and antihelmintic drugs, antibacterials, antibiotics, antimicrobials and other antiseptics, anticoagulants, anticonvulsants, antidepressants and antidiabetic, antifungal and antigout drugs. The modified waxes may also be used to form matrices for the release of household, agricultural and/or marine active agents. Wax encapsulation of the additive results in particles which are inert even to drugs and active agents which would otherwise cause an unwanted reaction, because the active agent and additive are at least predominantly if not completely separated in the final drug formulation by the inert wax.

Under certain circumstances, the wax and additive and active agent may all be combined in the melt, with cooling and granulation of the admixture. The directly compressible, active-agent containing granules have multiple uses because they have good flow properties. They may be compressed directly into dosage forms; they may be stored and shipped for use elsewhere; they can be remelted for reformulation at the same or a different location; they may be dry admixed with other directly compressible diluents; they may be encapsulated/filled in hard gelatin capsules and they may be used in other applications along these lines.

It is believed, although there is no intent to be bound by this theory, that the melt addition of the wax(es) and additive(s) imparts good flow properties in one of two different ways. If the additive does not melt (finely divided silica, for example), it is believed that the silica particles form one or more cores within each wax granule, which core(s) adhesively react with and thus deactivate some (but not all) of the tackifying moieties of the wax molecules freed in the molten state. In addition, the presence of the one or more cores in the granule imparts a variable density throughout the granule, which variable density promotes flow due to rotational instability (tumbling effect) of the granules If the additive does melt, it is believed that the admixed additive aligns and binds at the molecular level with some (but again not all) of the tackifying moeities of the wax, reducing tack and improving the flow properties of the granular product The modified wax granules demonstrate good cohesive strength upon compression, but typically do not adhere to each other under their own weight. An additional benefit afforded by the present wax modification is the improvement, due to the presence of the wax, of the compression cohesion characteristics of the additive in at least some cases. Regardless of theory, of course, the granules of the present invention contain wax(es) and additive(s) combined in adherence patterns characteristic of the melt combination of the wax(es) and additive(s).

When active agents are added to the melt admixture of wax(es) and additive(s), naturally the active agent must be stable to the heat used to melt the wax. However, under the low melting heats (50°-85° C. preferably, or 50°-100° C.) of most waxes, many active agents are suitable. Suitable active agents include but are not limited to heat stable antibiotics, certain heat stable proteins and peptides, and any other pharmaceutical, household (including pesticides), agricultural or marine active agents which retain at least some chemical activity under the melt heat of the selected wax(es). Those skilled in the art appreciate that waxes having lower melting points should be selected for admixture with active agents having lesser heat stability. By contrast, when the active agent is directly compressed with the granules of the present invention after the granules have been cooled and formed, all types and varieties of active agents may be combined with the granules.

The invention will be understood with greater particularity in view of the following examples:

EXAMPLE 1

One hundred parts by weight of Gelucires ® glyceryl stearate (product code G64/02) were melted in a beaker contained within an oil bath held between 65°-70° C. Fifty parts by weight of 100-200 mesh size cellulose acetate particles were added to the molten wax with stirring, and the mixture was cooled to room temperature. The cooled mass was triturated to a powder in a glass mortar and pestle and the triturate was sieved into fractions. All fractions demonstrated good flow properties upon observation of mechanical transfer between glass, metal and paper receptacles. One fraction contained Gelucires ®/cellulose acetate granules having a mean diameter of 637.5 micrometers.

EXAMPLE 2

Example 1 was repeated, except 33 parts by weight cellulose acetate particles were used and the oil bath temperature was 75°-80° C.

EXAMPLE 3

Examples 1 and 2 were repeated, separately, with a 75°-85° C. oil bath and with addition of 150 parts by weight of procainamide hydrochloride (to the molten Gelucires ®/cellulose acetate admixture) adequate to yield a cooled mass containing a standard concentration of procainamide hydrochloride for direct preparation of oral dosage forms.

EXAMPLE 4

Example 1 was repeated with a 75°-95° C. oil bath and with the following constituents for each of nine formulas:

(a)
   62.5% by wt. carnauba wax
   12.5% by wt. Gelucires ® 44/14
   25.0% by wt. indomethacin (b)
   65.0% by wt. carnauba wax
   10.0% by wt. Gelucires ® 44/14
   25.0% by wt. indomethacin (c)
   62.5% by wt carnauba wax
   12.5% by wt. Gelucires ® 55/18
   25 0% by wt. indomethacin (d)
   70.0% by wt. carnauba wax
   5.0% by wt. Gelucirese 55/18
   25.0% by wt. indomethacin (e)
   62.5% by wt. carnauba wax
   12.5% by Wt. Gelucires ® 53/10
   25.0% by wt. indomethacin (f)
   50.0% by wt. carnauba wax
   12.5% by wt. Gelucires ® 44/14
   12.5% by wt. polyethylene glycol (PEG 4000)
   25.0% by wt. indomethacin (g)
   50.0% by wt. carnauba wax
   12.5% by wt. Gelucires ® 44/14
   12.5% by wt. polyethylene glycol (PEG 8000)
   25.0% by wt. indomethacin (h)
   50.0% by wt. carnauba wax
   12.5% by wt. Gelucires ® 55/18
   2.5% by wt. polyethylene glycol (PEG 4000)
   5.0% by wt. indomethacin (i)
   50.0% by wt. carnauba wax
   12.5% by wt. Gelucires ® 55/18
   12.5% by wt. polyethylene glycol (PEG 8000)
   25.0% by wt. indomethacin Each of the above formulations, when melt-combined, cooled and granulated, exhibited good flow properties under observation. Sieved fractions having a mean particle size of 425 micrometers (40 mesh) and 850 micrometers (20 mesh), separately, were free-flowing and well-suited to capsule-filling applications. Sieved fractions could have been prepared containing granules as small as 38 microns and as large as 1 millimeter.

EXAMPLE 5

Example 1 was repeated with a 75°-95° C. oil bath using the following constituents and amounts:

(a)
   50.0% by wt. carnauba wax
   12.5% by wt. Compritol ® hydro
   12.5% by wt. microcrystalline cellulose ("Avicel")
   25.0% by wt. propranolol hydrochloride (b)
   50.0% by wt. carnauba wax
   12.5% by wt. Gelucires ® 64/02
   12.5% by wt. microcrystalline cellulose ("Avicel")
   25.0% by wt. propranolol hydrochloride (c)
   50.0% by wt. carnauba wax
   12.5% by wt. Gelucires ® 62/05
   12.5% by wt. microcrystalline cellulose ("Avicel")
   25.0% by wt. propranolol hydrochloride (d)
   50.0% by wt. carnauba wax
   12.5% by wt. Gelucires ® 48/09
   12.5% by wt. microcrystalline cellulose ("Avicel")
   25.0% by wt. propranolol hydrochloride (e)
   55.0% by wt. carnauba wax
   7.5% by wt. Gelucires ® 48/09
   12.5% by wt. microcrystalline cellulose ("Avicel")
   25.0% by wt. propranolol hydrochloride (f)
   48.5% by wt. carnauba wax
   14.0% by wt. Gelucires ® 64/02
   12.5% by wt. microcrystalline cellulose ("Avicel")
   25.0% by wt. propranolol hydrochloride (g)
   45.0% by wt. carnauba wax
   17.5% by wt. Compritol ® hydro
   12.5% by wt. microcrystalline cellulose ("Avicel")
   25.0% by wt. propranolol hydrochloride (h)
   50.0% by wt. carnauba wax
   12.5% by wt. Gelucires ® 64/02
   12.5% by wt. microcrystalline cellulose ("Avicel")
   25.0% by wt. propranolol hydrochloride Each of the above formulations, when melt-combined, cooled and granulated, exhibited good flow properties.

Although the invention has been described above with respect to particular constituents and methods, the invention is to be limited only insofar as is set forth in the accompanying claims.

We claim:

1. A modified-wax, directly compressible diluent consisting of:
   1) at least one wax selected from the group consisting of carnauba wax, beeswax, glyceride esters, fatty acid esters, hydrogenated vegetable oils, hydrogenated animal fats, stearyl alcohols, stearyl alcohol derivatives, polyethylene glycols, and polyethylene glycol derivatives, and
   2) at least one wax-modifying composition selected from the group consisting of polyethylene glycol, polyvinyl alcohol, polyvinyl pyrrolidone, polyvinyl acetate, ethylene vinyl acetate polymer, acrylic polymer, acrylic copolymer cellulose compositions, cellulose derivatives, polyethylene oxide, poly(methylvinylether/maleic acid), carbomers, vinyl chloride vinyl acetate polymers, finely divided silica, particulate sodium chloride, particulate sodium bromide, particulate calcium chloride, particulate calcium bromide, particulate sugar, particulate calcium phosphate, particulate calcium carbonate, particulate oyster shells and ground bone meal, wherein said wax and said wax-modifying composition are present in the ratio of 1:4–4:1 and further wherein said wax and said wax-modifying composition are combined in adherence patterns characteristic of the melt combination of said wax and said wax-modifying composition.

2. A modified-wax, directly compressible diluent consisting of:

1) at least one wax selected from the group consisting of carnauba wax, beeswax, glyceride esters, fatty acid esters, hydrogenated vegetable oils, hydrogenated animal fats, stearyl alcohols, stearyl alcohol derivatives, polyethylene glycols, and polyethylene glycol derivatives, and 2) at least one wax-modifying composition selected from the group consisting of polyethylene glycol, polyvinyl alcohol, polyvinyl pyrrolidone, polyvinyl acetate, ethylene vinyl acetate polymer, acrylic polymer, acrylic copolymer, cellulose compositions, cellulose derivatives, polyethylene oxide, poly(methylvinylether/maleic acid), carbomers, vinyl chloride vinyl acetate polymers, finely divided silica, particulate sodium chloride, particulate sodium bromide, particulate calcium chloride, particulate calcium bromide, particulate sugar, particulate calcium phosphate, particulate calcium carbonate, particulate oyster shells and ground bone meal, wherein said wax and said wax-modifying composition are present in the ratio of 1:9–9:1 and further wherein said wax and said wax-modifying composition are combined in adherence patterns characteristic of the melt combination of said wax and said wax-modifying composition.

* * * * *